US012788624B2

(12) United States Patent
Giuliani

(10) Patent No.: US 12,788,624 B2
(45) Date of Patent: Nov. 10, 2026

(54) THERMALLY CONTROLLED COLLAR

(71) Applicant: NEURON GUARD S.R.L., Modena (IT)

(72) Inventor: Enrico Giuliani, Modena (IT)

(73) Assignee: NEURON GUARD S.R.L., Modena (IT)

(*) Notice: Subject to any disclaimer, the term of this patent is extended or adjusted under 35 U.S.C. 154(b) by 153 days.

(21) Appl. No.: 18/689,406

(22) PCT Filed: Sep. 5, 2022

(86) PCT No.: PCT/IT2022/050244

§ 371 (c)(1),
(2) Date: Mar. 5, 2024

(87) PCT Pub. No.: WO2023/031983

PCT Pub. Date: Mar. 9, 2023

(65) Prior Publication Data

US 2025/0134703 A1 May 1, 2025

(30) Foreign Application Priority Data

Sep. 6, 2021 (IT) ........................ 102021000023027

(51) Int. Cl.
*A61F 7/00* (2006.01)

(52) U.S. Cl.
CPC ....... *A61F 7/007* (2013.01); *A61F 2007/0011* (2013.01); *A61F 2007/0054* (2013.01); *A61F 2007/0075* (2013.01); *A61F 2007/0086* (2013.01); *A61F 2007/0092* (2013.01); *A61F 2007/0096* (2013.01)

(58) Field of Classification Search
CPC ....... A61F 2007/0011–0012; A61F 2007/0054
See application file for complete search history.

(56) References Cited

U.S. PATENT DOCUMENTS

| | | | | |
|---|---|---|---|---|
| 9,486,354 | B2 * | 11/2016 | Maher | A61B 5/6812 |
| 12,011,382 | B2 * | 6/2024 | Maher | A61F 7/02 |
| 2005/0149153 | A1 | 7/2005 | Nakase | |
| 2008/0046047 | A1 | 2/2008 | Jacobs | |
| 2011/0172579 | A1 | 7/2011 | Chiu | |
| 2022/0142814 | A1 * | 5/2022 | Stegmann | A61F 7/0085 |

FOREIGN PATENT DOCUMENTS

| | | | | |
|---|---|---|---|---|
| CN | 107362461 A | 11/2017 | | |
| CN | 110420380 A | * 11/2019 | | A61F 7/10 |
| WO | 2014/057450 A1 | 4/2014 | | |

OTHER PUBLICATIONS

International Search Report and Written Opinion of the International Searching Authority for International Application No. PCT/IT2022/050244 issued Jan. 27, 2023 (8 sheets).

* cited by examiner

*Primary Examiner* — Joseph A Stoklosa
(74) *Attorney, Agent, or Firm* — Kratz, Quintos & Hanson, LLP

(57) ABSTRACT

The thermo-adjustable collar (10) designed to surround the neck (N) of a patient (P) comprises a flexible body (12) having, in a wrapped configuration, an annular shape, and temperature control means (13) associated with said flexible body (12) in a removable manner and connected to a control unit (16).

13 Claims, 2 Drawing Sheets

THERMALLY CONTROLLED COLLAR

FIELD OF THE INVENTION

The present invention concerns a thermo-adjustable collar that can generally be used to cool and/or heat specific zones of a person's neck, for example but not only a patient, in such a way as to induce a temperature variation in the blood circulation system that feeds the brain.

BACKGROUND OF THE INVENTION

Thermo-adjustable collars used on patients with severe trauma are known, both for immobilizing or limiting the movements of the head with respect to the spine, as well as for performing a heat treatment of the neck's circulatory system that supplies blood to the brain. An example of a thermo-adjustable collar known in the state of the art is described in the international patent application WO 2014/057450 by the same Applicant.

Generally, such collars have a rigid or semi-rigid annular support body able to wrap and immobilize the patient's neck. Such collars comprise a plurality of refrigeration elements for absorbing/supplying heat from/to the patient's neck.

Known solutions provide that such refrigeration elements are integrated into the body of the collar in an irremovable manner, presenting the coldest surface in direct or indirect contact with the patient's neck so as to regulate its temperature in a controlled manner.

The refrigeration elements known in the state of the art can comprise duly cooled Peltier cells which are managed by means of a control unit. It is evident that the refrigeration elements of this type are very complex, expensive and difficult to manage.

Furthermore, the thermo-adjustable collars are generally of the disposable type, because it is necessary to guarantee a high degree of sanitation before the collar is applied to the patient in order to prevent infections. Therefore, it is provided that a new collar is applied with each use, and that the one already used is disposed of without recovering any component. This entails high management costs, mainly due to the cost of the refrigeration elements.

In addition to this, it is necessary to completely change the collar also in the event of failure or malfunction of the refrigeration elements, because it is not possible to act in a targeted manner only on the broken or malfunctioning component.

Other known solutions provide that the refrigeration elements are of the type that can be "recharged" after a certain period of time, after which they have exhausted their cooling effect. The refrigeration elements are pre-emptively located and stored in a refrigeration unit that has to always be transported or positioned in proximity to the patient.

One disadvantage of these collars is that the replacement of the refrigeration elements during use is particularly complex and can be uncomfortable and painful for the patient. Furthermore, if the replacement of the refrigeration elements does not occur in the correct way and at the correct time, the temperature regulation therapy adopted to that point can be nullified. Furthermore, the replacement at cyclical time intervals requires the constant presence of a trained healthcare professional who supervises and monitors the patient and the operating status of the collar.

Another disadvantage that is encountered in known thermo-adjustable collars is that the body of the collar is particularly rigid because it has to integrate and/or support the refrigeration elements. This causes inconvenience in applying the collar to the patient's neck as well as a consequent difficulty in removing it.

PURPOSES OF THE INVENTION

One purpose of the invention is to improve the state of the art.

Another purpose of the invention is to provide a thermo-adjustable collar which has much lower production and management costs than those of the state of the art.

Another purpose of the invention is to provide a collar that allows to cool and/or heat the structure that wraps a patient's neck in an extremely rapid, uniform, targeted and controlled manner.

According to one aspect of the invention, a thermo-adjustable collar is provided in accordance with the characteristics of claim 1.

BRIEF DESCRIPTION OF THE DRAWINGS

Other characteristics and advantages of the present invention will become more apparent from the detailed description of some preferred but not exclusive embodiments of a thermo-adjustable collar, shown as a non-limiting example in the attached drawings wherein.

DETAILED DESCRIPTION OF A PREFERRED EXAMPLE EMBODIMENT

Figure 1:
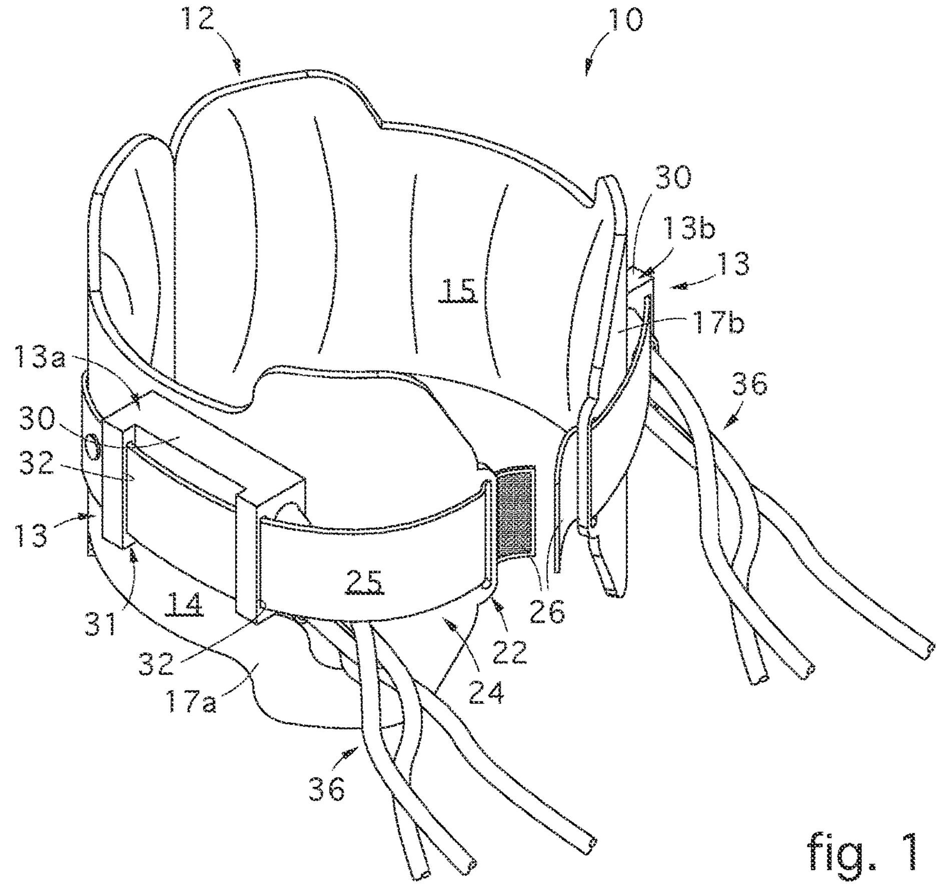
FIG. 1 is a schematic perspective view of a thermo-adjustable collar, according to the present invention.

With reference to FIG. 1, a thermo-adjustable collar, hereafter also just collar, 10 intended to be worn around the neck N of a patient P, comprises a flexible body 12 that has, in a wrapped configuration, an overall annular shape.

The flexible body 12 can advantageously be of the single use type, that is, disposable, but in other embodiments it can be of the reusable type.

The collar 10 can advantageously be wrapped around the neck N of a person who has suffered a traumatic event, such as a road accident for example, or other clinical condition in which there is a need to regulate the cerebral temperature, but it can also be advantageously used in a sports context. For example, the collar 10 can be wrapped around the neck N of a pilot in motor racing or sports racing competitions, in which the person is destined to endure very high temperatures for several hours.

The collar 10 also comprises temperature control means 13 associated with the flexible body 12 in a removable manner, and a control unit 16 configured to manage the temperature control means 13. In the example given here, the temperature control means 13 are associated with an external wall 14 of the flexible body 12 in a removable manner.

Here and hereafter in the description, by external wall 14 we meant the wall of the flexible body 12 opposite an internal wall 15 which, during use, is disposed in direct contact with the neck N of the patient P.

In other words, the flexible body 12 is interposed between a heat exchange surface of the temperature control means 13 and the neck N of the patient P, acting, as will become clearer in the following, as an interface for the absorption/emission of heat.

The flexible body 12 comprises one or more bags that have a shape and size such as to wrap the structures the temperature of which is to be controlled, in this specific case the surface of the neck N.

In the example given here, the flexible body 12 comprises two bags, indicated with reference numbers 17*a* and 17*b*.

The bags 17*a*, 17*b* are advantageously made of biocompatible material, such as PTU ether or other similar or comparable materials.

The bags 17*a*, 17*b* can have the shape of a band. Each bag 17*a*, 17*b* can, for example, have, as standard sizes, a height equal to approximately the axial extension of the neck N of the patient P and a length equal to approximately half the circumference of the neck N of the patient P.

Each bag 17*a*, 17*b* can be selectively filled with a conductive liquid L. The temperature of the liquid L is regulated by conduction by means of the temperature control means 13.

Each bag 17*a*, 17*b* is provided with a duct 19 and a valve 20 through which each bag 17*a*, 17*b* can be filled with the desired quantity of liquid L. Specifically, an aperture (not shown) is made on each bag 17*a*, 17*b*, which is suitable to receive one end of the duct 19. Preferably, the connection between the duct 19 and the aperture produces a sealed coupling, and it can comprise a threaded mechanical connection, or a pressure connection. Depending on the volume of liquid introduced into the bags 17*a*, 17*b*, their stiffness is determined, which can be chosen as a function of the specific condition of the patient P or the type of therapy to be performed. For example, the collar 10 can be initially applied to the neck N of the patient P with the bags 17*a*, 17*b* empty, and they can be filled immediately afterward in the desired manner.

The valve 20 can be of the one-way, or non-return, or two-way type, so as to allow to empty the bags 17*a*, 17*b* before eliminating them at the end of the treatment.

The bags 17*a*, 17*b* can have section widenings, or convex zones 18, which, during use, are disposed in correspondence with the blood vessels to be reached in such a way as to increase the contact surface with the neck N and improve the heat exchange efficiency of the collar 10. During use, two of such convex zones 18 are disposed in the lateral-frontal position of the neck N, while the other two are disposed in the lateral-posterior position.

Figure 2:
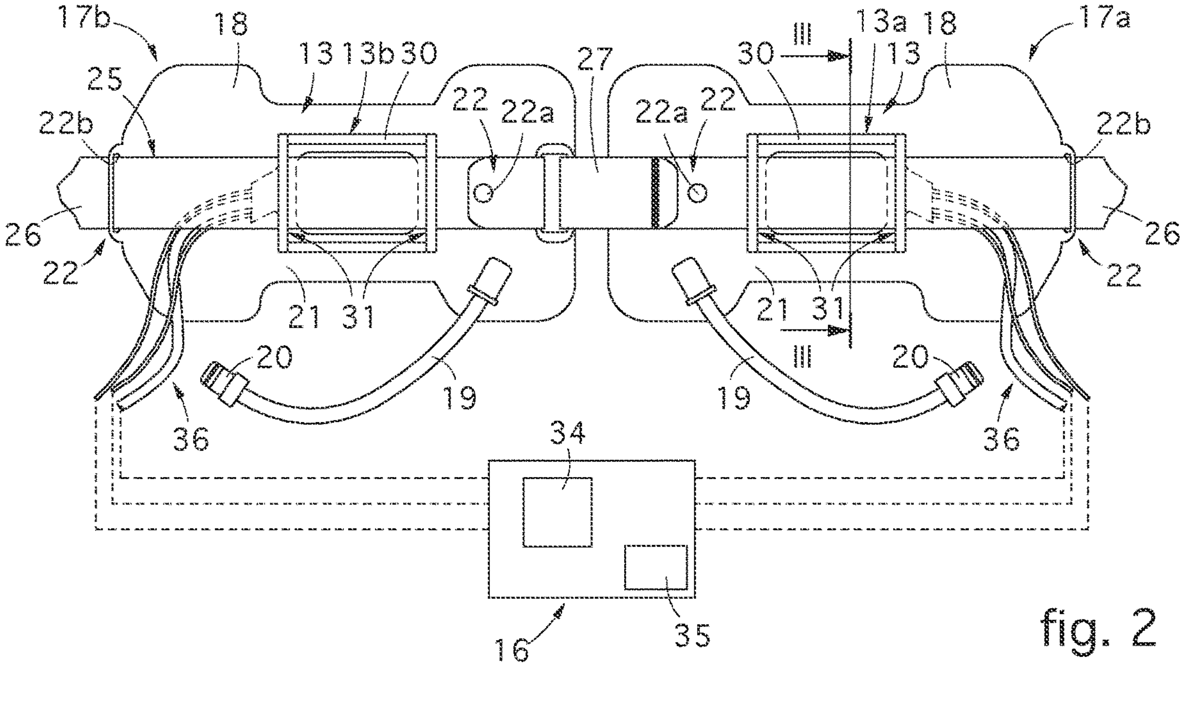
FIG. 2 is a rear schematic view of the collar of FIG. 1 in a fully open configuration.

As can be seen in FIG. 2, each bag 17*a*, 17*b* comprises two convex zones 18, disposed at opposite ends of the bag, separated by a central portion 21. The height of the convex zones 18 is greater than the height of the central zone 21.

The duct 19 enters the respective bag 17*a*, 17*b* in correspondence with one of the two convex zones 18.

The bags 17*a*, 17*b* can be provided with internal welds or channels which have the purpose of directing the liquid L from and toward the convex zones 18 as a result of the heat exchange with the neck N.

The shape of the bags 17*a*, 17*b* is such as to minimize the pressure on the neck, so as not to compress the underlying blood vessels in a clinically significant manner. If this compression were to occur, it could potentially cause serious harm to the patient, with the risk of nullifying the therapeutic benefits obtained with the temperature management.

The flexible body 12 is provided on the external wall 14 with quick coupling means 22 on which a support structure 24 for the temporary support of the temperature control means 13 couples in a removable manner.

In particular, the bags 17*a*, 17*b* are provided, on their respective external wall 14, with buttons 22*a* and slots 22*b* on which the support structure 24 is coupled. In this specific case, the slots 22*b* are made in a single body with the bags 17*a*, 17*b*, but they could be produced in many different ways.

The support structure 24 can comprise a strap 25 which wraps the bags 17*a*, 17*b* externally, connecting them to each other.

The strap 25 is attached to the bags 17*a*, 17*b* in a removable manner, by means of the buttons 22*a* and the slots 22*b* inside which it is made to pass. After the collar 10 has been used, the strap 25 can be released and removed so that it can be reused, or it can be of the disposable type, like the flexible body 12, and eliminated together with it once the collar 10 is no longer used.

The strap 25 is made of a flexible but non-extensible material, such as PVC for example, or other similar or comparable materials.

Along its development, the strap 25 is provided with closure devices 26 and with possible adjustment devices 27 for adjusting the size of the collar 10, which is determined directly on the neck N of the patient P.

In a closed configuration of the collar 10, the closure devices 26 can be positioned at the front while the adjustment devices 27 can be placed at the rear.

In the example described here, the closure devices 26 are configured as a tear strip, preferably elastic, while the adjustment devices 27 are configured as an elastic band or ring.

The temperature control means 13 can comprise at least two temperature control units 13*a*, 13*b*, hereafter also refrigeration and/or heating units, each of which consists of the combination of a thermoelectric module, in this specific case a Peltier cell 28, and an exchanger module, in this specific case a liquid exchanger 29, functional to keep the Peltier cell 28 efficient.

Figure 3:
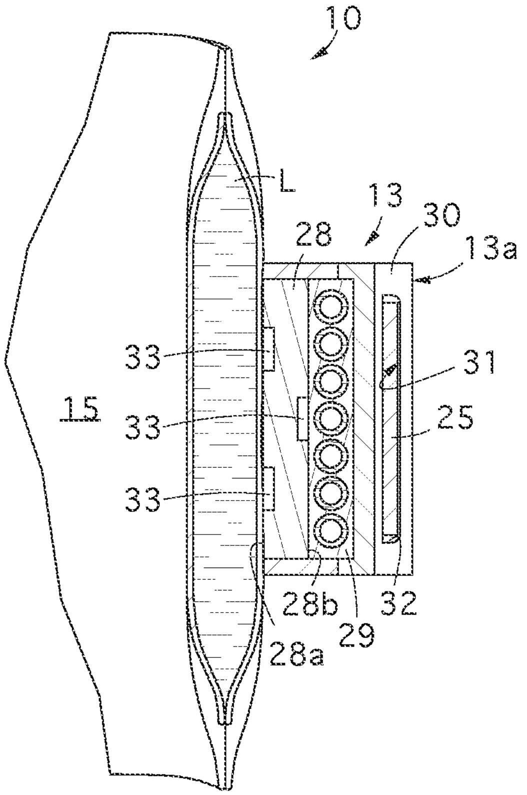
FIG. 3 is a section view along the line III-III of FIG. 2.
Figure 4:
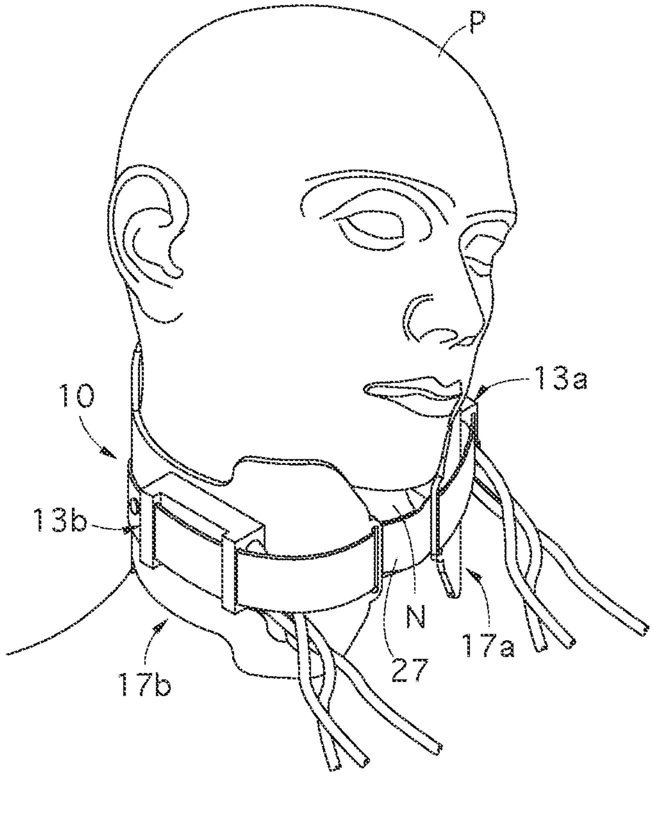
FIG. 4 is a perspective view of the collar of FIG. 1 in a configuration worn on a patient's neck.

As is known, the Peltier cell 28 has two heat exchange surfaces 28*a*, 28*b* (FIG. 3), namely a first surface 28*a*, which during use faces the underlying bag 17*a*, 17*b*, and a second surface 28*b*, opposite and parallel to the first surface 28*a*, which is in direct or indirect contact with the liquid exchanger 29. By suitably managing the current that passes through the Peltier cell 28, it is possible to control the temperatures of the first and second surfaces 28*a*, 28*b*.

Preferably, the first surface 28*a* which comes into contact with the bag 17*a*, 17*b* has a conductivity of at least 150 W/m K, while the other surfaces have a conductivity of about 0.25 W/m K.

In the example described here, there are two refrigeration and/or heating units 13*a*, 13*b*, each of which can reach, independently of each other, a temperature comprised in a range between about 3° C. and about 42° C.

The presence of two refrigeration and/or heating units 13*a*, 13*b* combined with the flexible body 12 filled with the liquid L makes the heat exchange very effective and reduces the complexity and cost of manufacturing the collar 10 compared to those of the state of the art.

The refrigeration and/or heating unit 13*a*, 13*b* is preferably positioned along the strap 25 so as to be disposed on the respective bag 17*a*, 17*b* in correspondence with the central portion 21. In this way, during use, the refrigeration and/or heating units 13*a*, 13*b* are disposed in a lateral position on the neck N of the patient P, where the curvature of the latter is less pronounced, thus being able to guarantee a more extensive contact and therefore a more effective regulation of the heat, while reducing the pressure on the neck. A pressure higher than 20 $cmH_2O$ on the neck, in fact, can be an obstacle to the venous return of blood from the brain, causing potentially even very severe damage to the patient.

The refrigeration and/or heating unit 13*a*, 13*b* comprises a shell 30 which contains the Peltier cell 28 and the liquid exchanger 29.

The shell 30, which can for example be made in two parts, is provided with releasable coupling means 31 for the temporary connection with the strap 25 or directly with the bags 17*a*, 17*b*.

The releasable coupling means 31 can, by way of example, comprise at least one through element 32, preferably two, as in the example described in FIGS. 1-4.

Alternatively, the releasable coupling means 31 can comprise magnetic or ferromagnetic elements able to couple to corresponding ferromagnetic or magnetic elements.

By way of example, the magnetic elements can be configured as magnets. In one embodiment, three magnetic elements can be provided applied directly on each of the bags 17*a*, 17*b*, each of them cooperating with a respective magnetic element disposed in a correlated position on each refrigeration and/or heating unit. The distribution of the magnetic elements is uniform, so as to guarantee a firm connection between the bag 17*a*, 17*b* and the corresponding refrigeration and/or heating unit 13*a*, 13*b*.

Other types of releasable coupling means 31 can comprise coupling means of the mechanical type, for example sliding, interlocking, or pressure coupling means.

The refrigeration and/or heating unit 13*a*, 13*b* is provided with temperature detection sensors 33, of which at least one, preferably at least two, is disposed on the first surface 28*a* which, during use, comes into contact with the bag, and at least one on the liquid exchanger 29, in order to monitor the efficiency of the heat removal.

The detection sensors 33 are operatively connected to the control unit 16, which can manage the refrigeration and/or heating units 13*a*, 13*b* both on the basis of the user's indications and also on the basis of the signals received from the detection sensors 33. The control unit 16 allows to manage both the desired temperature value for each refrigeration and/or heating unit 13*a*, 13*b*, and also the temperature variation ramp.

The control unit 16 comprises pumping and dissipation means 34 configured to make a heat exchange liquid circulate inside the liquid exchangers 29 of the refrigeration and/or heating units 13*a*, 13*b*, advantageously managing them in an independent manner.

The control unit 16 is configured to dissipate at least 400 W of heat.

The control unit 16 also comprises storage means 35 where all the operating data of the collar 10 and the alarms that have arisen are recorded, and where standardized programs for managing specific traumas or pathologies can be preloaded.

The control unit 16 can be powered both with an electric network and also, alternatively, with batteries so that it can also function during transport, making the collar 10 functional for any application whatsoever.

As stated, each refrigeration and/or heating unit 13*a*, 13*b* can be managed individually by the control unit 16 and receive a dedicated flow of heat exchange liquid by means of a three-lumen tube 36 specifically designed to minimize the loss of efficiency.

In practice it has been verified that the invention achieves the intended purposes.

The invention as conceived is susceptible to modifications and variants, all of which are within the scope of the inventive concept.

Furthermore, all the details can be replaced with other technically equivalent elements.

In their practical embodiment, any other materials, as well as shapes and sizes, can be used according to requirements, without departing from the field of protection of the following claims.

The invention claimed is:

1. Thermo-adjustable collar (10) designed to surround the neck (N) of a user (P) and comprising a flexible body (12), of the disposable or reusable type, configured to be filled with a thermally conductive liquid (L), which in a wrapped configuration has an annular shape and is configured to contact said neck (N), wherein said collar comprises temperature control means (13) for controlling the temperature of said liquid (L), of the reusable type, associated with said flexible body (12) in a removable manner and connected to a control unit (16) configured to control the thermo-regulation of said liquid (L), wherein said temperature control means (13) comprise at least two refrigeration and/or heating units (13*a*, 13*b*) and wherein said flexible body (12) comprises at least two bags (17*a*, 17*b*), each bag (17*a*, 17*b*) being selectively filled with said liquid (L) and being provided with a duct (19) and a valve (20) through which each bag (17*a*, 17*b*) can be filled with the desired quantity of liquid (L), wherein, depending on the volume of liquid introduced into the bags (17*a*, 17*b*), their stiffness is determined, each bag (17*a*, 17*b*) being in contact with a respective one of said refrigeration and/or heating units (13*a*, 13*b*) which thermo-regulate said liquid (L) by conduction/contact, each refrigeration and/or heating unit (13*a*, 13*b*) comprising an exchanger module configured as a liquid exchanger (29) and receiving a dedicated flow of heat exchange liquid, and each refrigeration and/or heating unit (13*a*, 13*b*) being managed individually by the control unit (16) in an independent manner.

2. The thermo-adjustable collar (10) as in claim 1, wherein said flexible body (12) is provided with quick coupling means (22) onto which a support structure (24) couples in a removable manner for the temporary support of said temperature control means (13).

3. The thermo-adjustable collar (10) as in claim 2, wherein said quick coupling means (22) are provided on an external wall (14) of said flexible body (12) so that said temperature control means (13) are associated with said external wall (14) in a removable manner.

4. The thermo-adjustable collar (10) as in claim 1, wherein each of the refrigeration and/or heating units (13*a*, 13*b*) comprises a thermoelectric module, configured as a Peltier cell (28).

5. The thermo-adjustable collar (10) as in claim 4, wherein said refrigeration and/or heating units (13*a*, 13*b*) are provided with respective temperature detection sensors (33), of which at least two are disposed on a first heat exchange surface (28*a*) of said Peltier cell (28) which, during use, is in contact with said flexible body (12), and at least one is disposed on said liquid exchanger (29).

6. The thermo-adjustable collar (10) as in claim 2, wherein said support structure (24) comprises a strap (25) that connects said bags (17*a*, 17*b*) to each other and is sized so that the flexible body (12) wraps around said neck (N).

7. The thermo-adjustable collar (10) as in claim 6, wherein each of the refrigeration and/or heating units (13*a*, 13*b*) comprises a thermoelectric module, configured as a Peltier cell (28) and wherein each refrigeration and/or heating unit (13_a_, 13_b_) comprises a shell (30) which contains said Peltier cell (28) and said liquid exchanger (29), said shell (30) being provided with releasable coupling means (31) for the temporary connection with said strap (25) or directly with said bags (17_a_, 17_b_).

8. The thermo-adjustable collar (10) as in claim 1, wherein said bags (17_a_, 17_b_) have section widenings, or convex zones (18), which, during use, are disposed in correspondence with blood vessels of said neck (N) in order to improve the heat exchange efficiency of said collar (10).

9. The thermo-adjustable collar (10) as in claim 8, wherein each of said bags (17_a_, 17_b_) comprises two convex zones (18), disposed at opposite ends of the bag, separated by a central portion (21), wherein the height of said convex zones (18) is greater than the height of said central zone (21).

10. The thermo-adjustable collar (10) as in claim 9, wherein said duct (19) enters a respective one of said bags (17_a_, 17_b_) in correspondence with one of said two convex zones (18).

11. The thermo-adjustable collar (10) as in claim 8, wherein each of said bags (17_a_, 17_b_) comprises internal welds or channels configured to direct said liquid (L) from and toward said convex zones (18).

12. The thermo-adjustable collar (10) as in claim 4, wherein each of said bags (17_a_, 17_b_) is connected to a respective one of said refrigeration and/or heating units (13_a_, 13_b_) by means of magnetic or ferromagnetic elements.

13. The thermo-adjustable collar (10) as in claim 1, wherein each of said valve (20) is a one-way or non-return valve, or a two-way valve also configured to allow to empty said liquid (L) from said flexible body (12).

* * * * *